United States Patent [19]

Cahoy

[11] 3,974,218
[45] Aug. 10, 1976

[54] PRE-EMERGENT CHEMICAL METHOD OF COMBATING UNWANTED VEGETATION

[75] Inventor: Roger P. Cahoy, Overland Park, Kans.

[73] Assignee: Gulf Research & Development Company, Pittsburgh, Pa.

[22] Filed: July 7, 1972

[21] Appl. No.: 269,857

Related U.S. Application Data

[60] Division of Ser. No. 88,166, Nov. 9, 1970, Pat. No. 3,707,366, which is a continuation-in-part of Ser. No. 9,419, Feb. 6, 1970, abandoned.

[52] U.S. Cl. .................... 260/558 P; 260/559 R; 260/562 R; 71/118
[51] Int. Cl.² ............... C07C 103/34; C07C 103/76
[58] Field of Search .................. 260/558, 559, 562

[56] References Cited
FOREIGN PATENTS OR APPLICATIONS
1,131,022  10/1968  United Kingdom .................. 71/118

OTHER PUBLICATIONS
Pagani et al., Farmaco Ed. Sci., vol. 24, pp. 1025–1037 (1969).

*Primary Examiner*—Harry I. Moatz
*Attorney, Agent, or Firm*—Carl A. Cline

[57] ABSTRACT

Undesired vegetation such as crabgrass, downey brome, giant foxtail, yellow foxtail, barnyard grass, flax and wild oats are combated by pre-emergent application of at least one compound belonging to a class of substituted N-benzyl amides of alkanoic and benzoic acids, particularly in the presence of seeds of such crops as cotton and soybeans. Illustrative of compounds which are very effective against several species of grasses as well as some broadleaf weeds in the presence of soybeans and cotton are two with the following structural formulas:

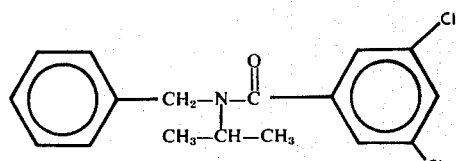

and

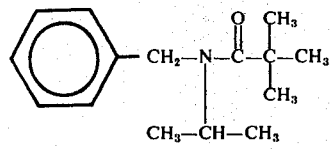

6 Claims, No Drawings

PRE-EMERGENT CHEMICAL METHOD OF COMBATING UNWANTED VEGETATION

This is a division of U.S. Pat. application Ser. No. 88,166 filed Nov. 9, 1970, now U.S. Pat. No. 3,707,366 which is a continuation-in-part of abandoned application Ser. No. 9,419, filed Feb. 6, 1970.

DESCRIPTION OF INVENTION

This is a continuation-in-part of U.S. Pat. application Ser. No. 9419, filed Feb. 6, 1970 in which there was disclosed a class of N-benzyl carboxamides which have selective pre-emergent herbicidal activity, both against grasses and some broadleaf weeds, but without causing substantial injury to either soybeans or cotton. In most instances these compounds were disclosed to also cause no more than slight injury to grain crops such as corn and wheat.

The class of compounds disclosed in the prior application was fairly broad. However, I have subsequently discovered that the presence of unsubstituted benzyl and isopropyl groups on the amide nitrogen is more desirable than was previously recognized and 3,5-disubstituted benzamides are particularly effective and useful.

The new class of compounds which have been found to have particularly desirable selective pre-emergent herbicidal activity may be described as having the following general structural formula,

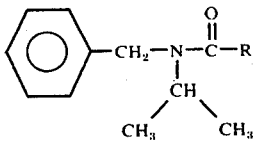

in which R is selected from tertiary butyl and the structure having the formula

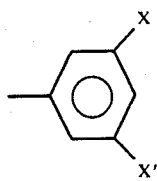

in which X and X' may be alike or unlike and are selected from the group consisting of chloro, bromo, methyl and methoxy substituents, with the additional provision that either one of X or X' may be hydrogen.

By way of illustration, effective compounds include the specific compounds listed below.

N-Benzyl-N-isopropylpivalamide (b.p. 87°C/0.07 mm)

N-Benzyl-N-isopropyl-3-chlorobenzamide (m.p. 62–64°C)

N-Benzyl-N-isopropyl-3-bromobenzamide ($n_D^{25}$ 1.5822)

N-Benzyl-N-isopropyl-3,5-dichlorobenzamide (m.p. 96–98°C.)

N-Benzyl-N-isopropyl-3,5-dimethylbenzamide (viscous oil, $n_D^{27}$ 1.5457)

N-Benzyl-N-isopropyl-3,5-dimethoxybenzamide (viscous oil, $n_D^{24}$ 1.5448)

N-Benzyl-N-isopropyl-3,5-dibromobenzamide (m.p. 89–90°C.)

Selection of the 3 and 5- position substituents on the benzoyl structure is apparently a critical factor, since the 3,5-dinitro, ditert.-butyl, diiodo and bis trifluoromethyl compounds are so deficient in herbicidal activity as to have no practical utility for this purpose. The corresponding unsubstituted benzoyl compound possesses some activity but at an application rate of 1 lb per acre is fails to kill any of the species tested and is therefore definitely inferior to the class of compounds disclosed herein.

SYNTHESIS OF THE HERBICIDES

The herbicides of this invention may be readily synthesized from commercially available substances by means of procedures of the type exemplified below:

Preparation of N-benzyl-N-isopropylpivalamide

A one-liter reaction flask fitted with a power stirrer, heating mantle, dropping funnel, thermometer, water-cooled condenser and drying tube was charged with 149.2 g (1.0 mole) N-benzyl-N-isopropylamine, 350 ml of benzene and 111.1 g (1.1 mole) of triethylamine. The dropping funnel contained 126.6 g (1.05 mole) of pivalyl chloride which was added dropwise to the stirred reaction mixture. After the addition was completed, the reaction mixture was stirred and heated at 75–80° for 18 hours. The mixture was cooled and the amine-salt was collected on a vacuum filter. The filtrate was transferred to a separatory funnel and extracted with water which was followed by dilute aqueous hydrochloric acid. The organic phase was dried over sodium sulfate. After removing the drying agent, the solvent was evaporated. The liquid residue was transferred to a pot which was appropriately fitted for a simple vacuum distillation. The forecut material proved to be mainly trimethylacetyl chloride and trimethylacetic acid. The product fraction weighed 188.6 g, b.p. 86-87/0.07 mm, $n_D^{25}$ 1.5074.

Anal. Calcd. for $C_{15}H_{23}NO$: C, 77.21; H, 9.93; N, 6.00

Found: C, 76.96; H, 9.89; N, 6.21

Preparation of N-benzyl-N-isopropyl-3,5-dichlorobenzamide

A small reaction flask fitted with a magnetic stirrer, heating mantle, thermometer, water-cooled condenser and drying tube was charged with 25.0 g (0.131 mole) of 3,5-dichlorobenzoic acid, 75 ml of thionyl chloride and 6 drops of N,N-dimethylformamide. The reaction mixture was stirred and refluxed for 18 hours. The excess thionyl chloride was removed by evaporation. The liquid residue was charged to a pot fitted with a short column and appropriately equipped for vacuum distillation. The 3,5-dichlorobenzoyl chloride product cut weighed 24.1 g, b.p. 63°–5°C/0.3 mm.

A 500-milliliter reaction flask equipped with a magnetic stirrer, heating mantle, dropping funnel, air-cooled condenser and drying tube was charged with 7.8 g (0.052 mole) of N-benzyl-N-isopropylamine, 400 ml of benzene and 7.0 g (0.07 mole) of triethylamine. The dropping funnel contained 10.5 g (0.05 mole) of 3,5-dichlorobenzoyl chloride which was added dropwise to the stirred reaction mixture. After the addition was completed, the reaction mixture was stirred and heated at 60°–65°C for 18 hours. The mixture was cooled and the amine salt was collected on a vacuum filter. The filtrate was transferred to a separatory funnel and extracted with water which was followed by dilute aqueous hydrochloric acid.

The organic phase was dried over sodium sulfate. After removing the drying agent, the solvent was evaporated. The solid residue was warmed with hexane, cooled and the product was collected. There was obtained 9.9 g of white crystalline solid, m.p. 96°–98°C.

Anal. Calcd. for $C_{17}H_{17}Cl_2NO$: C, 63.37; H, 5.32; N, 4.35

Found: C, 63.13; H, 5.18; N, 3.95

In a similar manner, the following compounds were prepared.

N-benzyl-N-isopropyl-3,5-dimethylbenzamide

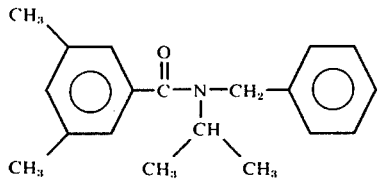

Viscous oil, $n_D^{27}$ 1.5457

Anal. Calcd. for $C_{19}H_{23}NO$: C, 81.09; H, 8.23; N, 4.97

Found: C, 80.73; H, 7.84; N, 5.20

N-benzyl-N-isopropyl-3,5-dimethoxybenzamide

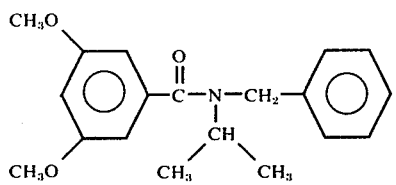

Viscous oil, $n_D^{24}$ 1.5448

Anal. Calcd. for $C_{19}H_{23}NO_3$: C, 72.82; H, 7.40; N, 4.47

Found: C, 73.87; H, 7.33; N, 4.10

N-benzyl-N-isopropyl-3,5-dibromobenzamide

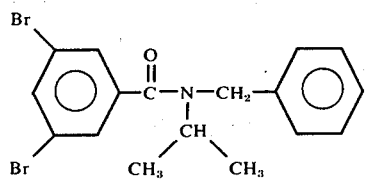

m.p. 89°–90°

Anal. Calcd. for $C_{17}H_{17}Br_2NO$: C, 49.68; H, 4.17; N, 3.41

Found: C, 49.85; H, 4.24; N, 3.28

Formulation of the Herbicides

The herbicides of this invention may be conveniently formulated in organic solvents, as dry granular materials or in water-dispersible form for use in aqueous sprays. By way of illustration, N-benzyl-N-isopropylpivalamide may be formulated as about a 24 percent solution along with about 66 percent xylene or other solvent and 10 percent of a surfactant such as Agrimul A-300 or N-300, Sponto934 or 234, Atlox 3408F or Triton X-180 or a mixture of Triton X-180 and X-190 or other dispersant or emulsifier which is recommended and approved for use with herbicides. Analyses of these surfactants are available from the agencies which approve the materials for agricultural use. In general, blends of both ionic and nonionic surfactants are desirable because they confer good water dispersibility on the formulations over a wide range of temperature, water hardness and other conditions. A blend of equal parts of Atlox 3404 and 3403F, for example, has been found to be particularly useful.

A granular formulation may be made by dissolving the herbicide in acetone and spraying the acetone solution on finely divided attapulgite while agitating as a rolling bed in a revolving drum. The resulting granules which form are then dried to remove the solvent.

PRE-EMERGENT USE OF THE HERBICIDES

A solution of each active compound was prepared by dissolving 290 mg. of the compound to be tested in 200 ml of acetone. Disposable expanded polystyrene trays about 2½ inches deep and about one square foot in area were prepared and seeded with a variety of species of plant seeds, then sprayed with the acetone solution at the rate of active chemical per acre of sprayed area shown in the following table and were then covered with about ¼ inch of soil. One group of trays which had been seeded with alfalfa, brome, flax, oats, radishes and sugar beets was held at 75°F day temperature; another seeded with corn, coxcomb, cotton, crabgrass, millet and soybeans was held at 85°F. Twenty-one days after seeding and treatment the plantings were examined and degree of herbicidal effect was rated according to the schedule below.

DEGREE

0 = no effect
1 = slight effect
2 = moderate effect
3 = severe effect
4 = maximum effect (all plants died)

| | Rate Lbs/A. | Crabgrass | Coxcomb | Brome | Millet | Soybean | Cotton | Alfalfa | Oats | Corn | Flax | Radish | Sugar Beet |
|---|---|---|---|---|---|---|---|---|---|---|---|---|---|
| | 5 | 4 | 4 | 4 | 4 | 1 | 0 | 4 | 4 | 2 | 4 | 4 | 4 |
| | 2 | 4 | 4 | 4 | 4 | 0 | 0 | 4 | 4 | 1 | 4 | 4 | 2 |
| | 1 | 4 | 4 | 4 | 4 | 0 | 0 | 4 | 3 | 1 | 3 | 3 | 2 |

-continued

| Structure | Rate Lbs/A. | Crab-grass | Cox-comb | Brome | Mil-let | Soy-bean | Cot-ton | Al-fal-fa | Oats | Corn | Flax | Ra-dish | Su-gar Beet |
|---|---|---|---|---|---|---|---|---|---|---|---|---|---|
| Ph-CH₂-N(CH(CH₃)₂)-C(O)-(3,5-diCH₃-C₆H₃) | 5 | 4 | 4 | 4 | 4 | 1 | 0 | 4 | 2 | 1 | 4 | 4 | 4 |
| | 2 | 4 | 4 | 4 | 4 | 1 | 0 | 4 | 1 | 1 | 4 | 4 | 3 |
| | 1 | 4 | 4 | 4 | 4 | 0 | 0 | 4 | 0 | 0 | 2 | 1 | 1 |
| Ph-CH₂-N(CH(CH₃)₂)-C(O)-(3,5-diOCH₃-C₆H₃) | 5 | 4 | 4 | 4 | 4 | 0 | 0 | 4 | 2 | 1 | 4 | 2 | 4 |
| | 2 | 4 | 2 | 1 | 4 | 0 | 0 | 4 | 1 | 0 | 4 | 1 | 1 |
| | 1 | 4 | 1 | 1 | 4 | 0 | 0 | 4 | 1 | 0 | 4 | 1 | 1 |
| Ph-CH₂-N(CH(CH₃)₂)-C(O)-(3,5-diBr-C₆H₃) | 5 | 4 | 4 | 4 | 4 | 0 | 0 | 4 | 4 | 1 | 3 | 4 | 1 |
| | 2 | 4 | 4 | 4 | 4 | 0 | 0 | 4 | 4 | 1 | 3 | 4 | 1 |
| | 1 | 4 | 1 | 4 | 4 | 0 | 0 | 4 | 3 | 1 | 2 | 3 | 0 |
| Ph-CH₂-N(CH(CH₃)₂)-C(O)-C(CH₃)₃ | 5 | 4 | 1 | 4 | 4 | 2 | 0 | 1 | 4 | 4 | 2 | 1 | 1 |
| | 2 | 4 | 1 | 4 | 4 | 1 | 0 | 1 | 4 | 3 | 1 | 0 | 0 |
| | 1 | 3 | 1 | 4 | 3 | 0 | 0 | 0 | 4 | 1 | 1 | 0 | 0 |
| Ph-CH₂-N(CH(CH₃)₂)-C(O)-(3-Cl-C₆H₄) | 5 | 4 | 4 | 4 | 4 | 2 | 0 | 4 | 4 | 3 | 3 | 4 | 4 |
| | 2 | 4 | 4 | 3 | 4 | 1 | 0 | 4 | 2 | 2 | 3 | 3 | 4 |
| | 1 | 4 | 4 | 3 | 4 | 0 | 0 | 4 | 2 | 1 | 2 | 3 | 4 |
| Ph-CH₂-N(CH(CH₃)₂)-C(O)-(3-Br-C₆H₄) | 5 | 4 | 4 | 3 | 4 | 0 | 0 | 4 | 2 | 2 | 2 | 2 | 4 |
| | 2 | 4 | 4 | 1 | 4 | 0 | 0 | 4 | 1 | 1 | 1 | 1 | 1 |
| | 1 | 4 | 4 | 1 | 2 | 0 | 0 | 1 | 0 | 0 | 1 | 2 | 1 |

As can be seen from the tabulated data from illustrative controlled experiments, the novel herbicides in general are highly toxic to several of the test species, both certain broadleaf weeds and noxious grasses. Because of their pre-emergent selectivity toward undesired species, they are particularly suited for use in combating specific annual weeds in the presence of crops such as corn, sugar beets, cotton and soybeans. These compounds also find use in combating annual grasses in perennial pastures and for treatment of soil prior to laying perennial grass sod. A few of the compounds which possess selective toxicity to only a very small number of species are particularly useful in herbicide mixtures, making up for the deficiencies of other herbicides, yet not endangering desirable crop plants.

The method of the present invention also provides a means of combating annual grasses in rice fields. For example, N-benzyl-N-isopropylpivalamide, N-benzyl-N-isopropyl-3,5-dimethylbenzamide and N-benzyl-N-isopropyl-3,5-dichlorobenzamide may be applied at rates between about ¼ lb and 3 lb per acre to control barnyard grass in fields of rice. Although there is some difference in activity, all of these compounds may be used effectively if applied at an appropriate rate. In an illustrative procedure, rice plants were cut off to a height of about 4 inches and were transplanted into quart size plastic containers of moist soil. The containers were seeded with barnyard grass. Part of the containers were sprayed with aqueous dispersions of herbicide immediately. Part were sprayed after 3 days, so that part of the barnyard grass seed would have time to germinate. In addition, one of the herbicides was applied in the form of clay granules containing 5 percent herbicide. Four weeks after application of herbicides the results were rated according to the schedule which appears above. The results are tabulated below.

| | Control of Barnyard Grass in Rice | | | |
|---|---|---|---|---|
| | | Application Time | | |
| | | At 0 Days | | After 3 Days | |
| | Application Rate lb/A. | Barnyard Grass | Rice | Barnyard Grass | Rice |
| N-Benzyl-N-isopropyl-3,5-dimethylbenzamide | 2 | 4 | 1 | 4 | 1 |
| | 1 | 4 | 0 | 4 | 0 |
| | ½ | 2 | 0 | 3 | 0 |
| N-Benzyl-N-isopropyl-3,5-dichlorobenzamide | 2 | 4 | 1 | 4 | 0 |
| | 1 | 4 | 0 | 4 | 0 |
| | ½ | 3 | 0 | 4 | 0 |

-continued

| | | Control of Barnyard Grass in Rice | | | |
|---|---|---|---|---|---|
| | | At 0 Days | | After 3 Days | |
| | Application Rate lb/A. | Barnyard Grass | Rice | Barnyard Grass | Rice |
| N-Benzyl-N-isopropyl-pivalamide | 1 | 4 | 3 | 4 | 2 |
| | ½ | 2 | 0 | 4 | 1 |
| Same herbicide, as 5% granules | 1 | 3 | 2 | 4 | 3 |
| | ½ | 1 | 1 | 4 | 1 |

I claim:
1. N-Benzyl-N-isopropylpivalamide.
2. N-Benzyl-N-isopropyl-3-chlorobenzamide.
3. N-Benzyl-N-isopropyl-3-bromobenzamide.
4. N-Benzyl-N-isopropyl-3,5-dimethylbenzamide.
5. N-Benzyl-N-isopropyl-3,5-dimethoxybenzamide.
6. N-Benzyl-N-isopropyl-3,5-dibromobenzamide.

* * * * *